United States Patent
Boudreau et al.

(10) Patent No.: US 6,849,774 B2
(45) Date of Patent: Feb. 1, 2005

(54) SEPARATION OF DIENES FROM OLEFINS USING IONIC LIQUIDS

(75) Inventors: Laura C. Boudreau, Houston, TX (US); Michael S. Driver, San Francisco, CA (US); Curt L. Munson, Oakland, CA (US); William L. Schinski, San Rafael, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 529 days.

(21) Appl. No.: 10/037,044

(22) Filed: Dec. 31, 2001

(65) Prior Publication Data

US 2003/0125599 A1 Jul. 3, 2003

(51) Int. Cl.$^7$ .............................. C07C 7/00; C07C 7/10; C07C 7/148; C07C 7/152

(52) U.S. Cl. ....................... 585/809; 585/810; 585/843; 585/845; 585/849; 585/850; 208/219; 208/223

(58) Field of Search ................................. 585/809, 810, 585/843, 845, 849, 848, 850; 208/219, 223

(56) References Cited

U.S. PATENT DOCUMENTS

| | | |
|---|---|---|
| 3,304,341 A | 2/1967 | Weiner et al. |
| 3,401,112 A | 9/1968 | Dunlop et al. |
| 3,407,789 A | 10/1968 | Hallee et al. |
| 3,647,682 A | 3/1972 | Rabo et al. |

(List continued on next page.)

FOREIGN PATENT DOCUMENTS

GB    1001886    8/1965

OTHER PUBLICATIONS

Malz Kr., Richard. *Chemical Ind.*, "Catalysis of Organic Reactions," 68:249–263 (1996) Marcel Dekker, Inc., New York.

Enderby, J., *J. Phys. Condens. Matter*, "Ionic Liquids: recent progress and remaining problems", 5: (supp 34B) B99–B106 (1993) Institute of Physics Publishing, UK.

(List continued on next page.)

*Primary Examiner*—Walter D. Griffin
*Assistant Examiner*—Tam N. Nguyen
(74) *Attorney, Agent, or Firm*—Sarita R. Kelley

(57) ABSTRACT

Methods for separating di-olefins from mono-olefins, and olefins from non-olefins such as paraffins, oxygenates and aromatics; are provided. The methods use metal salts which complex both mono-olefins and di-olefins, but which selectively complex di-olefins in the presence of mono-olefins. The metal salts are dissolved or suspended in ionic liquids, which tend to have virtually no vapor pressure. Preferred salts are Group IB salts, more preferably silver and copper salts. A preferred silver salt is silver tetrafluoroborate. A preferred copper salt is silver CuOTf. Preferred ionic liquids are those which form stable solutions, suspensions or dispersions of the metal salts, which do not dissolve unwanted non-olefins, and which do not isomerize the mono- or di-olefins. The equivalents of the metal salt can be adjusted so that di-olefins are selectively adsorbed from mixtures of mono- and di-olefins. Alternatively, both mono- and di-olefins can be adsorbed, and the mono-olefins selectively desorbed. The latter approach can be preferred when non-olefins are also to be separated. The mono- and di-olefin-containing mixture can be in the gas phase or in the liquid phase. The flow of mono- and di-olefin-containing mixture over/through the ionic liquid can be, for example, co-current, counter-current, or staged in stirred tanks, with countercurrent being preferred.

56 Claims, 2 Drawing Sheets

Liquid-Liquid Extraction

U.S. PATENT DOCUMENTS

| | | |
|---|---|---|
| 3,679,782 A | 7/1972 | La Hue et al. |
| 3,758,403 A | 9/1973 | Rosinski et al. |
| 3,820,955 A | 6/1974 | Woebcke |
| 4,128,595 A | 12/1978 | Montgomery |
| 4,347,392 A | 8/1982 | Cosyns et al. |
| 4,499,055 A | 2/1985 | DiNicolantonio et al. |
| 4,571,442 A | 2/1986 | Cosyns et al. |
| 4,762,956 A | 8/1988 | Liu et al. |
| 4,814,067 A | 3/1989 | Gartside et al. |
| 4,828,679 A | 5/1989 | Cormier, Jr. et al. |
| 4,980,053 A | 12/1990 | Li et al. |
| 5,059,732 A | 10/1991 | Cosyns et al. |
| 5,326,465 A | 7/1994 | Yongqing et al. |
| 5,712,171 A | 1/1998 | Zambias et al. |
| 5,811,621 A | 9/1998 | van Dijk |
| 5,859,304 A | 1/1999 | Barchas et al. |
| 6,339,182 B1 | 1/2002 | Munson et al. |

OTHER PUBLICATIONS

Freemantle, M., *Chemical and Engineering News*. "Designer Solvents", 32–37 (Mar. 30, 1998) American Chemical Society, Washington, D.C.

Gordon, C., et al., *J. Mater. Chem.,* "Ionic liquid crystals: hexafluorophosphate salts", 8: 2627–2636 (1998) The Royal Society of Chemistry, Cambridge, UK.

Seddon, K., *J. Chem. Tech. Biotechnol.,* "Ionic Liquids for Clean Technology". 68: 351–356 (1997) John Wiley & Sons Ltd., UK..

Welton, T., *Chem. Rev.,* "Room–Temperature Ionic Liquids. Solvents for Synthesis and Catalysis". 99:2071–2084 (1999) American Chemical Society, Washington, D.C.

Silver Complexation of Dienes

Complexation Ratio = 1.5

Process Options

Extractive Distillation

Liquid-Liquid Extraction

SEPARATION OF DIENES FROM OLEFINS USING IONIC LIQUIDS

FIELD OF THE INVENTION

The present invention is in the field of organic separations, in particular separation of di-olefins from mono-olefins, and olefins from non-olefins, using olefin-complexing metal salts dissolved, dispersed or suspended in ionic liquids.

BACKGROUND OF THE INVENTION

There are many product streams in the field of petroleum chemistry which include both mono-olefins and di-olefins, for example resulting from hydrocracking, olefin oligomerization and paraffin dehydrogenation. For a variety of reasons it is desirable to separate mono-olefins from di-olefins. For example, normal alpha mono-olefins such as 1-butene, 1-hexene and 1-octene are valuable products; and product specifications often require relatively low levels of di-olefins (also known as dienes). When paraffins are dehydrogenated to form olefins and subsequently used in alkylation chemistry, di-olefin by-products from the dehydrogenation step produce undesired products in the alkylation step. Di-olefins are also known to poison some catalysts and need to be removed before certain reactions can be performed. Di-olefins themselves are often valuable products, but must be separated from unwanted mono-olefins. For example, di-olefins are often used as crosslinking agents and in Diels-Alder reactions.

Methods for selectively converting di-olefins to mono-olefins have been developed. For example, one commercially licensed process employs a selective, supported hydrogenation catalyst to selectively remove di-olefins by converting them to mono-olefins. However, there are several limitations to this type of process. Normal alpha olefins (NAO) may be isomerized to internal olefins in the presence of the catalyst. Hydrogenation can also cause side reactions such as formation of branched hydrocarbons. Some of the olefins may also be hydrogenated, forming paraffins. Further, the hydrogenation process does not remove paraffins, which are often present in the product streams. Additionally, known catalysts are toxic, corrosive, volatile and environmentally harmful.

Another method for separating di-olefins from mono-olefins involves distillation. However, di-olefins are difficult to remove from mono-olefins by distillation because they tend to be extremely close in relative volatility. Therefore, distillation requires a large number of stages and/or high reflux ratios. Paraffins are also difficult to separate from olefins via distillation because there is only a small difference in relative volatility between a paraffin and the corresponding olefin with the same number of carbons. Given purity requirements for commercially viable olefins, it is difficult and expensive to achieve the required separation using distillation.

Therefore, while the olefins are extremely commercially valuable, the commercially available methods for separating them are expensive, toxic, or both. None of the known processes provide a facile method for obtaining relatively high purity olefin components from olefin-containing streams such as cracked gases. It is a difficult separation to achieve economically by distillation. It is also difficult to control the side reactions and the migration of double bonds which occur in catalytic hydrogenation.

It would be advantageous to have economical methods for separating di-olefins from mono-olefins, and, preferably, separating both di-olefins and mono-olefins from non-olefins such as paraffins. It would also be advantageous to have such methods which also limit the formation of unwanted products, such as branched hydrocarbons, paraffins, and olefins with internal double bonds. The present invention provides such methods.

Ionic liquids are a category of compounds which are made up entirely of ions and are liquid at or below process temperatures. Usually, such compounds produce solids with high melting points (commonly known as 'molten salts'). Ionic liquids differ from 'molten salts', in that they have low melting points, and are liquid at process temperatures. Moreover, they tend to be liquid over a very wide temperature range, with a liquid range of up to about 500° C. Ionic liquids are generally non-volatile, with no effective vapor pressure. Most are air and water stable, and are good solvents for a wide variety of inorganic, organic, and polymeric materials.

Ionic liquids are used herein to dissolve, suspend, disperse or otherwise immobilize olefin-complexing metal salts. When a mixture containing mono-and di-olefins is contacted with such an immobilized olefin-complexing metal salt, di-olefins are selectively complexed over mono-olefins, forming a metal salt/olefin complex. Since ionic liquids are non-volatile, the non-complexed mono-olefins may be easily separated via distillation or other conventional methods. Furthermore, the di-olefins may be readily desorbed and recovered from the metal salt/olefin complex, allowing the ionic liquid-metal salt solution to be recovered and recycled. Mono-olefins may also be complexed, allowing facile separation of non-olefins followed by selective desorption of mono- and di-olefins.

SUMMARY OF THE INVENTION

Methods for separating di-olefins from mono-olefins and, optionally, non-olefins such as paraffins, oxygenates and aromatics, are provided. The methods use metal salts which complex both mono-olefins and di-olefins, but which preferentially complex di-olefins in the presence of mono-olefins with a high degree of selectivity. The metal salts are dissolved, dispersed or suspended in ionic liquids. Preferred salts are Group IB salts, more preferably silver or copper salts. A preferred silver salt is silver tetrafluoroborate, although Pd salts may be preferred for separating olefins higher than $C_8$. Preferred ionic liquids are those which form stable solutions, suspensions or dispersions of the metal salts, which do not dissolve unwanted non-olefins, and which do not isomerize the mono- or di-olefins.

The olefins can be recovered from the ionic liquids by a number of regeneration options including any combination of thermal regeneration (increasing the solution temperature to reverse the complexation) and pressure swing regeneration (reducing the pressure to reverse the complexation). Sweep gases may also be used in the regeneration step.

In one embodiment, the method involves selectively complexing di-olefins in the presence of mono-olefins, and separating the non-complexed mono-olefins from the complexed di-olefins. The selective complexation is performed by adjusting the equivalents of the metal salt in the ionic liquid such that essentially only di-olefins are complexed. If non-olefins are present and it is desired to separate them from the mono-olefins, the mono-olefins can be complexed and then the non-complexed non-olefins are separated from the olefins. The separation can be effected by distillation, decantation or other means known to those of skill in the art.

In another embodiment, both mono- and di-olefins are complexed, and any non-olefins can be separated, for example via distillation or decantation. The complexed mono- and di-olefins are separated by staged desorption. Mono-olefins are not as tightly bound to the complexating agent as the di-olefins, and can be desorbed more readily. The desorption conditions typically involve distillation under vacuum. After the mono-olefins are desorbed, the di-olefins can then be desorbed, generally at high temperatures and/or lower pressures than the mono-olefins.

The present invention contemplates that the mono- and di-olefin-containing mixture can be in the gas phase or in the liquid phase. In the liquid phase, conventional liquid/liquid extraction equipment, such as mixer-settlers, can be used. The flow of the mono- and di-olefin-containing mixture over/through the ionic liquid can be, for example, co-current, counter-current, or staged in stirred tanks, with countercurrent being preferred.

Silver complexes can be poisoned by various compounds, including sulfur compounds, cyanides and acetylides. Silver acetylides also pose potential risk of explosion. Accordingly, these compounds should be removed before the mixtures are brought into contact with the ionic liquids. Methods for removing such contaminants are well known to those of skill in the art.

One embodiment of this invention involves a method for separating mono-olefins from a mixture including mono-olefins and di-olefins wherein the mixture is contacted with an ionic liquid solution, suspension or dispersion of an olefin-complexing metal salt capable of selectively complexing the di-olefin over the mono-olefin. The mixture is maintained in contact with the ionic liquid solution for sufficient time to selectively complex the di-olefin over the mono-olefin to form a metal salt/olefin complex. The non-complexed mono-olefin is then separated from the overall mixture. The di-olefin may then be desorbed from the metal salt/olefin complex.

In another embodiment, a mixture comprising di-olefins and mono-olefins is contacted with an olefin-complexing metal salt dissolved, dispersed, or suspended in an ionic liquid. The mixture is maintained in contact with the olefin-complexing metal salt for sufficient time to complex the mono-olefins and di-olefins with the olefin-complexing metal salt to form a metal salt/olefin complex. The mono-olefins are then selectively desorbed from the metal salt/olefin complex. The di-olefin may then be desorbed from the metal salt/olefin complex.

In another embodiment, this invention involves a method for separating mono-olefins and/or di-olefins from a mixture including mono-olefins, di-olefins and non-olefins. The mixture, comprising a di-olefin, a mono-olefin and a non-olefin, is contacted with an ionic liquid solution, suspension or dispersion of an olefin-complexing metal salt capable of selectively complexing the di-olefin over the mono-olefin. The mixture is maintained in contact with the ionic liquid solution for sufficient time to complex the mono-olefins and di-olefins with the olefin-complexing metal salt to form a metal salt/olefin complex. The non-complexed non-olefins are separated, and then the mono-olefin is selectively desorbed from the metal salt/olefin complex. The di-olefin may then be desorbed from the metal salt/olefin complex.

Another embodiment of this invention involves contacting a mixture comprising di-olefins, mono-olefins and non-olefins with an olefin-complexing metal salt dissolved, dispersed or suspended in an ionic liquid. The mixture is maintained in contact with the olefin-complexing metal salt for sufficient time to selectively complex the di-olefins over the mono-olefins to form a first metal salt/olefin complex. The non-complexed mono-olefins and non-olefins are separated. Then, the di-olefins may be desorbed from the first metal salt/olefin complex. Next, the non-complexed mono-olefins and non-olefins are contacted with the olefin-complexing metal salt and maintained in contact with such olefin-complexing metal salt for sufficient time to complex the mono-olefins to form a second metal salt/olefin complex. Then, the non-complexed non-olefins are separated. The mono-olefins may then be desorbed from the metal salt/olefin complex.

DETAILED DESCRIPTION OF THE INVENTION

Figure 1:
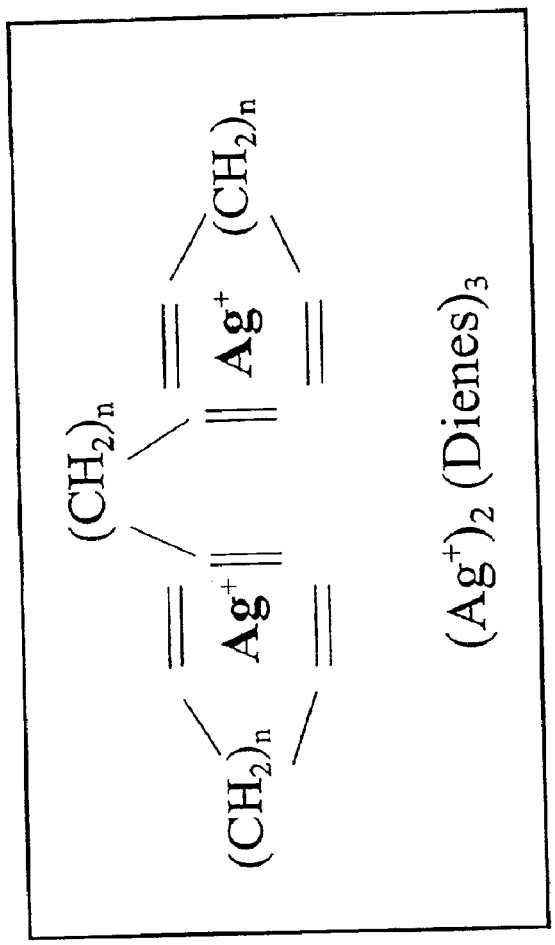
FIG. 1 is a graph showing the complexation of three di-olefins with two $Ag^+$ ions.

The present invention is directed to methods for separating di-olefins from mono-olefins, and olefins from non-olefins. The compositions include ionic liquid solutions, suspensions or dispersions of metal salts which complex mono- and di-olefins. The di-olefins can be selectively complexed in the presence of mono-olefins, or both di-olefins and mono-olefins can be complexed, and the mono-olefins selectively decomplexed in the presence of complexed di-olefins. Non-olefins, which are not complexed, tend to be immiscible in the ionic liquids and can be separated from any olefins, which are complexed. The complexed olefins tend to be either present in solution in the ionic liquids or precipitate out of solution and can be isolated, for example, via filtration.

Definitions

As used herein, the terms "adsorption" and "complexation" are used to describe the complexation of metal salts with olefinic species such as mono- and di-olefins. The term "desorption" is used to describe the decomplexation of the olefin from the olefin/metal salt complex. The term "adsorbents" is used to describe the olefin-complexing metal salts, alone or dissolved, suspended or dispersed in ionic liquids. The term "bottoms" is used to describe the portion of a process stream which collects in the bottom of a vessel during a fractionating process. The term "Group IB metal" is used to describe elements from Group IB (IUPAC Notation) of the periodic table of elements.

Mono-Olefins

The mono-olefins to be separated are preferably $C_{2-50}$ mono-olefins, more preferably $C_{2-20}$ mono-olefins. They may include other functional groups, such as hydroxy groups, carboxylic acid groups, heteroatoms, and the like, provided that such groups do not react with either the olefin-complexing salt or the ionic liquid so as to prevent an effective separation.

The mono-olefins can be used commercially to form a wide variety of products. For example, the mono-olefins can be used to form polyethylene, polypropylenes, polyisobutylene and other polymers, alcohols, vinyl chloride monomer, acrylonitrile, methyl tertiary butyl ether and other petrochemicals, and a variety of rubbers such as butyl rubber.

Sources of Mono- and Di-Olefins

Mono- and di-olefin mixtures can be derived from a variety of sources. One source of mono-olefin/di-olefin mixtures is from the dehydrogenation of paraffins over a suitable dehydrogenation catalyst. Other commercial sources of mono- and/or di-olefins include wax hydrocracking; ethylene and propylene derived from ethane, ethane/propane (EP) and flexi-crackers; fluid catalytic cracking (FCC) crackers; naptha crackers; ethenolysis of heavier internal olefins; and ethylene oligomerization. Olefins may also be produced in a Fischer-Tropsch process.

Catalysts and conditions for performing Fischer-Tropsch synthesis are well known to those of skill in the art, and are described, for example, in EP 0 921 184 A1, the contents of which are hereby incorporated by reference in their entirety. In the Fischer-Tropsch synthesis process, liquid and gaseous hydrocarbons are formed by contacting a synthesis gas (syngas) comprising a mixture of $H_2$ and CO with a Fischer-Tropsch catalyst under suitable temperature and pressure reactive conditions. The Fischer-Tropsch reaction is typically conducted at temperatures of about from 300° to 700° F. (149 to 371° C.) preferably about from 400° to 550° F. (204° to 228° C.); pressures of about from 10 to 600 psia (0.7 to 41 bars), preferably 30 to 300 psia (2 to 21 bars), and catalyst space velocities of about from 100 to 10,000 cc/g/hr., preferably 300 to 3,000 cc/g/hr.

The Fischer-Tropsch products may range from $C_1$ to $C_{200}+$ with a majority in the $C_5$–$C_{100}+$ range. The reaction can be conducted in a variety of reactor types for example, fixed bed reactors containing one or more catalyst beds, slurry reactors, fluidized bed reactors, or a combination of different type reactors. Such reaction processes and reactors are well known and documented in the literature. Slurry Fischer-Tropsch processes utilize superior heat (and mass) transfer characteristics for the strongly exothermic synthesis reaction and are able to produce relatively high molecular weight, paraffinic hydrocarbons.

Fischer-Tropsch chemistry tends to provide a variety of gaseous and liquid products, including unreacted synthesis gas, methane, and $C_{2-4}$ hydrocarbons (a mixture of olefins and paraffins). These gases are typically separated from the liquid products. The methane and other light paraffins can be recycled through an upstream synthesis gas generator. However, the light olefins tend to coke the catalysts, and need to be removed before the recycle gas is sent to the synthesis gas generator. The olefins are typically removed via cryogenic separation. The current invention allows for the removal of the olefins at ambient temperatures using ionic liquids.

Typically, about 75% of the $C_{2-8}$ products from Fischer-Tropsch synthesis are normal alpha-olefins (NAOs). Separation of the NAOs may be accomplished using conventional distillation. However, as noted above, there is only a small difference in relative volatility between an olefin and its corresponding di-olefin and corresponding paraffin with the same number of carbons. Therefore, distillation requires a large number of stages and/or high reflux ratios, and, as a result, is very expensive. The present invention provides an inexpensive method of separating mono-olefins, di-olefins and non-olefins using ionic liquids.

Other sources of olefins include processes for converting hydrocarbons at high temperature, including steam-cracking, catalytic cracking or deep catalytic cracking to produce relatively high yields of unsaturated hydrocarbons, for example ethylene, propylene, and butenes, are well known in the art. See, for example, U.S. Pat. No. 3,407,789 to Hallee et al., U.S. Pat. No. 3,820,955 to Woebcke, U.S. Pat. No. 4,499,055 to DiNicolantonio, U.S. Pat. No. 4,814,067 to Gartside et al., U.S. Pat. No. 4,828,679 to Cormier, Jr. et al., U.S. Pat. No. 3,647,682 to Rabo et al., U.S. Pat. No. 3,758,403 to Rosinski et al., U.S. Pat. No. 4,814,067 to Gartside et al., U.S. Pat. No. 4,980,053 to Li et al. and U.S. Pat. No. 5,326,465 to Yongqing et al., the contents of which are hereby incorporated by reference. Many of these also produce mono-olefins and di-olefins, which can be advantageously separated from the mono-olefins according to this invention.

Steam cracking is a petrochemical process sometimes used in refineries to produce olefinic raw materials (e.g. ethylene) form various feedstock for petrochemical manufacture. The feedstock range from ethane to vacuum gas oil, with heavier feeds giving higher yields of by-products such as naphtha. The most common feeds are ethane, butane, and naphtha. Stream cracking is carried out at temperatures of 1,500–1,600° F., and at pressures slightly above atmospheric.

In the cracking reaction of conventional fluid catalytic cracking (FCC) units of petroleum refineries, a hydrocarbon feedstock may be catalytically converted into a variety of products commonly known as slurry oil, heavy cycle oil, light cycle oil, naphtha, and various components lighter than naphtha, including paraffins and olefins. Of course, the particular products from any particular cat cracker unit depend on a variety of factors including the design and needs of the petroleum refinery. The products that include naphtha and lighter components are separated into various product streams. The products from the gas plant vary depending on the particular refinery design but commonly include naphtha, $C_4S$ (butylenes and butanes), propane, propylene, and a stream (commonly referred to as "fuel gas") that contains ethane and lighter components ($C_2$ and lighter), including light olefinic components such as ethylene and propylene.

The product yields from a conventional FCC unit vary depending on a wide range of design and operating parameters, such as feedstock quality, the amount of regenerated catalyst supplied to the riser reactor per volume or mass unit of feed, the temperature at which the cracking reaction takes place, the residence time of the feed in the riser reactor, and the like. The conventional fluid catalytic cracking unit may process one or more feedstocks.

Typical feedstocks may include atmospheric gas oils, heavier feedstocks from vacuum distillation units, and streams from other units such as cokers, visbreakers, hydrotreaters, and hydrocrackers.

Non-Olefins

Non-olefins present in the mono-olefin and di-olefin mixtures of this invention include paraffins, oxygenates, and/or aromatics, as well as hydrogen, water, carbon monoxide, carbon dioxide, acetylenics, sulfur and nitrogen-containing impurities and a wide variety of other materials which may be present in such mixtures.

Non-olefins such as paraffins and aromatics are often desirable products, particularly for use in distillate fuel compositions. However, it is often desirable to separate them from mono- and/or di-olefins, particularly if the mono- and/or di-olefins are desired products themselves.

Sulfur impurities are preferably removed from the feedstocks before they are added to the ionic liquid/metal salt solution, suspension or dispersion. This can be accomplished by hydrotreatment or other means well known to those of skill in the art.

Acetylene impurities are potentially undesirable, as they can form potentially explosive salts with various metals. Acetylene impurities are commonly removed by selective hydrogenation. The hydrogenation system may employ any of the catalysts well known to selectively hydrogenate acetylenics and dienes, for example acetylene, methyl acetylene and propadiene, as used, for example, in ethane crackers. Group VIII metal hydrogenation catalysts are the most commonly used and are preferred. Group VIII metal hydrogenation catalysts are ordinarily associated with a support, such as alumina. One preferred catalyst is a low surface area granular alumina impregnated with about 0.1 weight percent palladium. Examples of other catalysts which can be used include Raney nickel, ruthenium-on-aluminum, nickel arsenide-on-aluminum, and mixtures thereof. The catalysts ordinarily contain a Group VIII metal in an amount ranging from about 0.01 to about 1 percent by weight of the total catalyst. These and other catalysts are well known to those of skill in the art, and are described, for example, in U.S. Pat. No. 3,679,762 to La Hue et al., U.S. Pat. No. 4,571,442 to Cosyns et al., U.S. Pat. No. 4,347,392 to Cosyns et al. U.S. Pat. No. 4,128,595 to Montgomery, U.S. Pat. No. 5,059,732 to Cosyns et al., and U.S. Pat. No. 4,762,956 to Liu et al., the contents of which are hereby incorporated by reference.

Metal Salts

The metal salts useful according to this invention are selected from heavy metal ions which form chemical complexes with olefins, e.g., copper(I), silver(I), gold(I), nickel (II), platinum(II) and palladium(II). Silver (I) and copper(I) salts are particularly preferred, although Pd salts may be preferred for separating olefins higher than $C_8$. Useful silver(I) salts include silver acetate, silver nitrate, silver fluoride, silver tetrafluoroborate, and mixtures thereof. Silver tetrafluoroborate is particularly preferred.

Copper salts include copper halide salts, and can be buffered with a soluble organic nitrogen ligand, such as pyridine, piperidine, hydroxypropionitrile, diethylene triamine, acetonitrile, formamide and acetamide, derivatives thereof and mixtures thereof. Pyridine and/or hydroxypropionitrile are particularly preferred.

Salts such as iron (II), cobalt (II) and nickel (II) salts can also be used, provided they are effective at complexing the olefins. The concentration of metal salt in the ionic liquid is typically at least about 0.5 moles of salt per liter of solvent, and preferably at least about 2 moles of salt per liter of solvent.

It does not matter whether the salts are dissolved or merely suspended or dispersed in the ionic liquids for them to function as intended. Further, it tends not to matter whether the salts dissolve in, or are reacted with, the ionic liquids. For example, it appears that silver salts tend to dissolve in the ionic liquids, and copper salts tend to react with the ionic liquids, and both tend to complex the desired olefins.

The salts are able to complex the olefins at a variety of concentrations. At relatively high concentrations, the olefin/metal salt complex may precipitate from solution. If this precipitation is not desirable, more dilute solutions/dispersions should be used. However, this precipitation may be desirable and allow one to separate various olefins by precipitation and subsequent filtration.

Metal salts such as $Ag^+$ salts are believed to form complexes with di-olefins in which two double bonds from a first diolefin and a single double bond from a second di-olefin complex with a single $Ag^+$ ion, and the second double bond from the second di-olefin and two double bonds from a third di-olefin form a complex with a second $Ag^+$ ion. This type of complex is shown in FIG. 1.

Ionic Liquids

Ionic liquids are a category of compounds which are made up entirely of ions and are liquid at or below process temperatures. Usually, such compounds produce solids with high melting points, for example, above 450° C. These solids are commonly known as 'molten salts'. An example of a common 'molten salt' is NaCl, with a melting point of 800° C. Ionic liquids differ from 'molten salts', in that they have low melting points, for example, from −100° C. to 200° C. They tend to be liquid over a very wide temperature range, with a liquid range of up to about 500° C. Ionic liquids are generally non-volatile, with no effective vapor pressure. Most are air and water stable, and are good solvents for a wide variety of inorganic, organic, and polymeric materials. They are used herein to dissolve, suspend or disperse the olefin-complexing metal salts.

The properties of ionic liquids can be tailored by varying the cation and anion pairing. Ionic liquids and their commercial applications are described, for example, in J. Chem. Tech. Biotechnol, 68:351–356 (1997), Chem. Ind., 68:249–263 (1996), J. Phys. Condensed Matter, 5: (supp 34B):B99–B106 (1993); Chemical and Engineering News, Mar. 30, 1998, 32–37; J. Mater. Chem., *:2627–2636 (1998); and Chem. Rev., 99:2071–2084 (1999), the contents of which are hereby incorporated by reference.

Many ionic liquids are formed by reacting a nitrogen-containing heterocyclic ring, preferably a heteroaromatic ring, with an alkylating agent (for example, an alkyl halide) to form a quaternary ammonium salt, and performing ion exchange or other suitable reactions with various Lewis acids or their conjugate bases to form ionic liquids. Examples of suitable heteroaromatic rings include pyridine, substituted pyridines, imidazole, substituted imidazoles, pyrrole and substituted pyrroles. These rings can be alkylated with virtually any straight, branched or cyclic $C_{1-20}$ alkyl group, but preferably the alkyl groups are $C_{1-12}$ groups, since groups larger than this tend to produce low melting solids rather than ionic liquids. Various quaternary phosphonium compounds, thioethers, and cyclic and non-cyclic quaternary ammonium salts have also been used.

Counterions which have been used include chloroaluminate, bromoaluminate, gallium chloride, tetrafluoroborate, tetrachloroborate, hexafluorophosphate, nitrate, trifluoromethane sulfonate, methylsulfonate, p-toluenesulfonate, hexafluoroantimonate, hexafluoroarsenate, tetrachloroaluminate, tetrabromoaluminate, perchlorate, hydroxide anion, copper dichloride anion, iron trichloride anion, antimony hexafluoride, copper dichloride anion, zinc trichloride anion, as well as various lanthanum, potassium, lithium, nickel, cobalt, manganese, and other metal ions.

The ionic liquids can be neutral, basic or acidic. Neutral ionic liquids should be used if the desired mono- or di-olefins are not to be isomerized. If it does not matter whether the olefins are isomerized (and if the non-olefins are not acid-sensitive), either neutral or acidic ionic liquids can be used. Acidic ionic liquids can be used, for example, when the desired goal is to remove olefins and provide a paraffinic hydrocarbon stream, and when the olefins are unlikely to isomerize.

In one embodiment, a library of ionic liquids is prepared, for example by preparing various alkyl derivatives of the quaternary ammonium cation, and/or varying the associated anions. The acidity of the ionic liquids can be adjusted, for example, by varying the molar equivalents, types and combinations of Lewis and Bronsted acidic components.

Methods for Separating Olefins from Non-Olefins

Mono-olefins, di-olefins and mixtures thereof can be selectively removed from mixtures including the olefins and non-olefins, such as paraffins, oxygenates and aromatics. The olefins are brought into contact with olefin-complexing metal salts to form a metal salt/olefin complex. In one embodiment, di-olefins are selectively complexed over mono-olefins and non-olefins, with olefin-complexing metals salts which are dissolved, dispersed or suspended in an ionic liquid. The mono-olefins and non-olefins can then be separated from the complexed di-olefins, for example by decantation or distillation. Then, the mono-olefins can be complexed, and the non-complexed non-olefins separated from the complexed mono-olefins. Both, the di-olefins and mono-olefins, may be recovered from the metal salt/olefin complex by desorption.

In another embodiment, the mono- and di-olefins are both complexed, and the non-olefins are removed. Then, the mono-olefins can be selectively desorbed, separating them from the complexed di-olefins. Finally, the complexed di-olefins can be desorbed, typically at higher temperatures and/or lower pressures than those at which the mono-olefins are desorbed.

The flow of olefin-containing mixtures over/through the ionic liquid can be, for example, co-current, counter-current, or staged in stirred tanks. Countercurrent is preferred as it is the most efficient.

Methods for Selectively Complexing Di-Olefins Over Mono-Olefins

According to this invention, metal salts selectively complex di-olefins over mono-olefins. This selective complexation can be exploited to selectively remove di-olefins from a mixture including di-olefins and mono-olefins. Since both mono-olefins and di-olefins complex with the metal salts, where di-olefins are to be complexed with a high selectivity, it will be important to adjust the equivalents of the metal salt to essentially complex only the di-olefins. Mixtures containing di-olefins and mono-olefins can be contacted with a solution, suspension or dispersion of an olefin-complexing metal salt in an ionic liquid, for example by direct addition, and the di-olefin can be selectively complexed by maintaining the olefin mixture in contact with the ionic liquid solution, suspension or dispersion, with or without agitation, for sufficient residence time to permit the complexation of the di-olefin, for example from about 1 minute to about 24 hours, or preferably about 10 minutes to about 8 hours. The di-olefin/metal salt complex tends to be either dissolved or suspended in the ionic liquid, or precipitate out. When the complex forms a precipitate, it can be removed, for example by filtration. When the complex is dissolved, dispersed or suspended in the ionic liquid, the non-complexed mono-olefin can be separated, for example by decantation or distillation. The complexed di-olefins can be isolated, for example by desorption. When the di-olefin has been removed, the enriched mono-olefin can be further purified or used directly, depending on whether there are additional contaminants.

Figure 2:
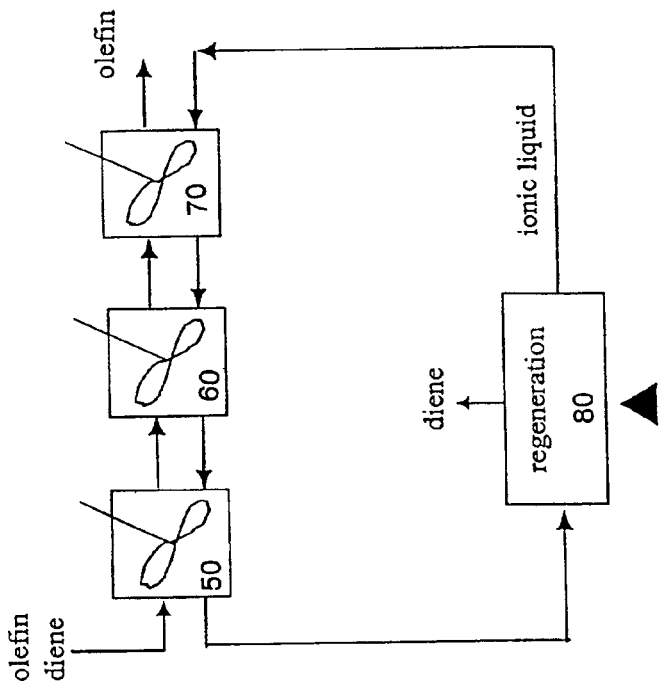
FIG. 2 is a schematic illustration of an extractive distillation process using the separation method described herein.

According to one embodiment, the method of this invention can be carried out via an extractive distillation process, as shown in FIG. 2. A mono-olefin/di-olefin containing mixture is added to a solution, suspension or dispersion of an olefin-complexing metal salt in an ionic liquid in a first distillation apparatus (10), and the di-olefin is maintained in contact with the ionic liquid for sufficient time to complex with the metal salt, for example from about 1 minute to about 24 hours, or preferably about 10 minutes to about 8 hours. After the complexation is essentially complete, for example after about 8 hours, the non-complexed mono-olefin is isolated via distillation (20). Then, the di-olefin/metal salt complex and ionic liquid are sent to a second distillation apparatus (30), where the di-olefin is desorbed and isolated via distillation (40). The bottoms form the second distillation apparatus, including the ionic liquid-metal salt solution, suspension or dispersion is then sent back to the first distillation apparatus.

Figure 3:
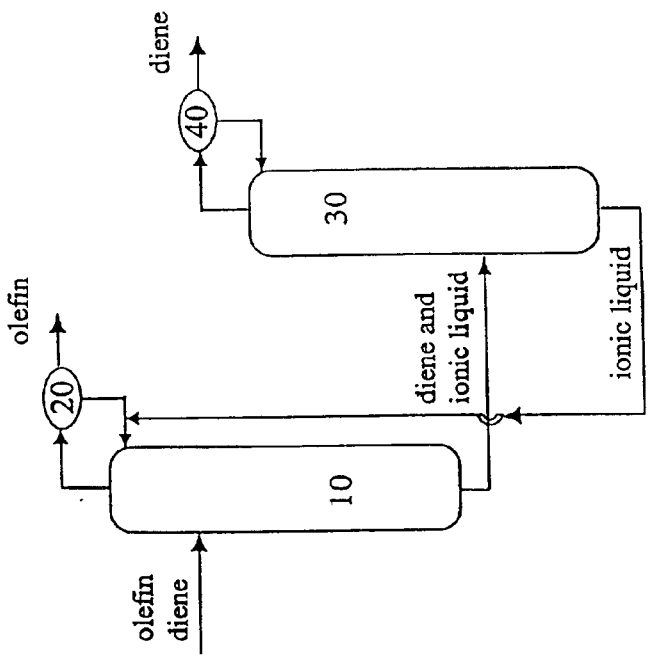
FIG. 3 is a schematic illustration of an liquid-liquid extraction process using the separation method described herein.

The method can also be carried out via a liquid-liquid extraction process, as shown in FIG. 3. A mono-olefin/di-olefin mixture is added to a solution, suspension or dispersion of an olefin-complexing metal salt in an ionic liquid in a first liquid mixer (50), and can be passed through a series of mixers (60 and 70), during which time the di-olefin is permitted to complex with the metal salt. After the complexation is essentially complete, for example after about 8 hours, the mixing is stopped, and the non-complexed mono-olefin is isolated via decantation. Then, the di-olefin/metal salt complex and ionic liquid are sent to a regeneration apparatus (80), where the di-olefin is desorbed and isolated via distillation. The bottoms from the regeneration apparatus, including the ionic liquid/metal salt solution, suspension or dispersion is then sent back to the series of mixers.

Non-complexed non-olefins, if present, can be removed from complexed olefins, for example by decantation or distillation. After di-olefins are removed, it may be desirable to complex the remaining mono-olefins and then remove any non-complexed non-olefins.

Methods for Desorbing Olefins from the Metal Salt-Complexes

According to the present invention, desorption is effected, preferably in a packed tower or flash drum, by dissociating the olefins from the olefin/metal salt complexes using a combination of increased temperature and lower pressure. At temperatures ranging from about 65° C. to about 110° C., preferably from about 70° C. to about 85° C., and pressures ranging from about 5 psig to about 50 psig, the mono-olefins readily dissociate from the metal salt complexes. Inexpensive quench water can conveniently be used as the heating medium for olefin stripper temperatures in the lower end of the range, as well as any other heating means known to those of ordinary skill in the art. The olefin stripper is preferably equipped with a water wash section in the top of the stripper to prevent entrainment of the scrubbing solution with the desorbed gases.

According to one embodiment, the olefin stripper or flash drum may include multi-stage stripping or flashing for increased energy efficiency. In such systems, the olefin-rich solution is flashed and stripped at progressively higher temperatures and/or lower pressures. The design of such systems is well known to those skilled in the art.

Once the mono-olefins are stripped from the ionic liquid solution, the di-olefins may then be desorbed in a reclaimer or regenerator. The stripped ionic liquid solution can be removed from the olefin stripper for reclaiming and recycling (regeneration). The reclaimer typically operates at a higher temperature than the olefin stripper. Typically, the temperature in the reclaimer ranges from about 100° C. to about 150° C., preferably from about 120° C. to about 140° C. The pressure ranges from about 5 psig to about 50 psig, preferably from about 10 psig to about 30 psig. The heating duty may be supplied by steam or any other means known to those skilled in the art. At these higher temperatures, di-olefins are dissociated from the metal salt complexes.

Methods for Selectively Desorbing Mono-Olefins Over Di-Olefins

According to this invention, the complexed mono-olefins selectively desorb over complexed di-olefins. This selective desorption can be exploited to selectively remove mono-olefins from a mixture including di-olefins and mono-olefins. Since both mono-olefins and di-olefins complex with the metal salts, the equivalents of the metal salt should be sufficient to complex both the mono- and di-olefins. Mixtures containing di-olefins and mono-olefins can be contacted with a solution, suspension or dispersion of an olefin-complexing metal salt in an ionic liquid, for example by direct addition, and the olefins can be complexed by maintaining the olefin mixture in contact with the ionic liquid solution, suspension or dispersion, with or without agitation, for sufficient residence time to permit the complexation of the olefins, for example from about 1 minute to about 24 hours, or preferably about 10 minutes to about 8 hours. Since the complexed olefins tend to be dissolved or suspended in the ionic liquid, any non-complexed non-olefins can be separated, for example by decantation or distillation.

After any non-olefins are separated, the complexed mono-olefins can be selectively desorbed from the metal salts. Mono-olefins are not as tightly bound as di-olefins, and when subjected to conditions of elevated temperature and reduced pressure, tend to desorb faster than diolefins. After the mono-olefins have desorbed from the metal salts, the temperature can be raised and/or the pressure decreased, and the di-olefins desorbed.

In one embodiment, a mixture includes di-olefins, mono-olefins and non-olefins such as paraffins and aromatics. The di-olefins can be selectively complexed and separated from this mixture as described above. Then, the mono-olefins can be complexed and separated from the non-olefins in a similar manner. Finally, both the mono- and di-olefins may be desorbed and recovered as described above.

Commercial Applications

There are many commercial applications for the separation technology described herein. For example, the technology can be used in ethane, ethane/propane and flexi-crackers to separate propadiene and propylene from propane, and then to separate propylene from propadiene.

Commercially, this is typically done using expensive distillation facilities. Such facilities are expensive because the boiling point difference between propylene and propadiene is small, and the separation must be done at very low temperatures and/or at very high pressures. The present separation method can be performed at room temperature and atmospheric pressure, using simple agitation. The major cost is due to the silver ions, which are recycled and reused.

Another commercial use is in the alkylation of aromatics, particularly where paraffins are dehydrogenated to form mixtures of mono- and di-olefins, and which also tend to include unreacted paraffins. The current technology for removing the di-olefins from the mono-olefins involves selective hydrogenation. The present methodology merely involves complexing the di-olefins with the metal ions in the ionic liquid. A preferred way to do this involves bubbling the olefin-containing stream, in the form of a gas rather than a liquid, through the ionic liquid.

Yet another commercial use is in olefin oligomerization, for example ethylene and propylene oligomerization. Such oligomerization reactions are commonly performed in normal alpha-olefin synthesis, and the separation methods can be used to upgrade the product stream to remove di-olefins.

A potential advantage of the methods described herein are that the di-olefins are not converted to mono-olefins, and can be purified and used in commercial applications where di-olefins are required, for example in Diels-Alder and similar chemistry.

Combinatorial Chemistry Approaches

Because of the wide applicability of this invention to a broad variety of separations, a combinatorial approach can be used to identify optimum ionic liquids and/or metal salts for separating the di-olefins from mono-olefins and non-olefins. An advantage to the combinatorial approach is that the choice of ionic liquid, metal salt and the like can be tailored to specific applications.

The scale of the separations in combinatorial chemistry is preferably in the range of about 1 mg to 200 g, more preferably between one mg and 10 g, although the scale can be modified as desired depending on the equipment used. Those of skill in the art can readily determine appropriate sets of reactions and reaction conditions to generate and/or evaluate the libraries of interest.

The ionic liquids can be laid out in a logical fashion in multi-tube arrays or multi-well plates in the form of arrays of ionic liquids. Preferably, the ionic liquids all have a central core structure, and have various modifications which permit the identification of structure-activity relationships with which to determine optimum compounds for a particular use. The metal salts or combinations thereof can also be laid out in a logical fashion, for example in arrays. In a preferred embodiment, an A×B array is prepared, with various combinations of ionic liquids and metal salts. However, it is also possible to evaluate a single ionic liquid with a plurality of metal salts, optionally at different concentrations, and then repeat the process as desired with a plurality of different ionic liquids.

The ability of the particular combination of ionic liquid and metal salt at performing a desired separation can be measured and correlated to specific combinations. The array can be ordered in such a fashion as to expedite synthesis and/or evaluation, to maximize the informational content obtained from the testing and to facilitate the rapid evaluation of that data. Methods for organizing libraries of compounds are well known to those of skill in the art, and are described, for example, in U.S. Pat. No. 5,712,171 to Zambias et al. Such methods can readily be adapted for use with the ionic liquids and metal salts described herein.

By screening multiple synthetic variations of a core molecule, the selection of the optimal candidate is more a function of the data collection method than the "rational" basis for selecting a useful ionic liquid and/or metal salt. The desired physical and chemical properties for the ionic liquid, when used as a solvent or dispersing agent for a particular metal salt, and for separating a particular product mixture, can be rapidly optimized, and directly correlated with the structural changes within a particular array or sub-array.

The ionic liquids are typically formed by first forming a desired (cyclic or non-cyclic) quaternary ammonium salt, and then combining the salt with an appropriate anion precursor (typically a metal salt such as aluminum chloride, zinc chloride, sodium hexafluorophosphate, sodium tetrafluoroborate, hexaflourophosphoric acid, tetrafluoroboric acid and the like). Side product salts can be removed, for example, by filtration. In cases where the anion precursor was an acid, the acid side product such as HCl can be removed by extraction or by gently heating the ionic liquid under vacuum.

The separations using the ionic liquids/metal salts in the libraries generally involve contacting appropriate mixtures of mono- and di-olefins to the tubes or wells in the multi-tube rack or multi-well plate, and allowing the olefin-complexation reactions to take place. Where a stoichiometric amount of metal complexing agent is used to selectively complex the di-olefins, the olefin layer can be analyzed, for example by gas chromatography (GC), for di-olefin concentration. Alternatively, where both mono-olefins and di-olefins are complexed, the complexed mixture can be subjected to conditions of relatively high temperature and low pressure, and as the olefins become desorbed from the metal salts, the products can be monitored as they are desorbed and the appearance of di-olefins monitored. Ideal results would be those in which mono-olefins are desorbed first, and where little or no mono-olefins are still being desorbed under conditions where the di-olefins begin desorbing. Here the desired separation involves selectively separating di-olefins, mono-olefins and non-olefins, the presence or absence of these components can be evaluated, for example using GC, to determine the success of the particular combination of ionic liquid and olefin-complexing metal salt.

Robotic arms and multi-pipet devices are commonly used to add appropriate reagents to the appropriate tubes in multi-tube racks, or wells in multi-well plates. When appropriate, the chemistry can be performed in an inert atmosphere. The tubes can each be covered with a rubber septum to avoid contamination, and the reagents added via injection.

In one embodiment, the separations are carried out via computer control. The identity of each of the ionic liquids and metal salts can be stored in a computer in a "memory map" or other means for correlating the data regarding the chemical reactions to the ionic liquids in the multi-tube racks or multi-well plates.

Alternatively, the chemistry can be performed manually, preferably in multi-tube racks or multi-well plates, and the information stored, for example on a computer.

Any type of multi-well plate or multi-tube array commonly used in combinatorial chemistry can be used. Preferably, the number of wells or tubes is in excess of 30, and there is a tube in at least 60 percent of the positions in each multi-tube array. The shape of the rack is not important, but preferably, the rack is square or rectangular. The tubes can be made, for example, from plastic, polymers, glass or metal, such as stainless steel, depending on the type of anions used in the ionic liquid or in the metal salt.

Any type of liquid handler that can add reagents to, or remove reagents from, the wells and/or tubes can be used. Many involve the use of robotic arms and robotic devices. Suitable devices are well known to those of skill in the art of combinatorial chemistry.

Any device that can take samples from the individual wells and/or tubes and analyze the resulting hydrocarbon phase can be used. Preferably, the device is a chromatographic device, such as an analytical or preparative scale high performance liquid chromatography (HPLC), GC or column chromatography, although other devices can be envisioned, depending on the chemistry performed. Since the ionic liquid is non-volatile, the sample is preferably taken from the hydrocarbon phase, which is immiscible with the ionic liquid.

Preferably, in those embodiments in which a chromatographic column (HPLC, GC or column chromatography) is used, the device has the ability to identify when the compound of interest is eluting from the column. Various means have commonly been used to identify when compounds of interest are eluting from a column, including ultra-violet (UV), infra-red (IR), thin layer chromatography (TLC), gas chromatography-mass spectrometry (GC-MS), free induction decay (FID), nuclear magnetic resonance (NMR), evaporative light scattering detector (ELSD), nitrogen detection and the like. Any of these means, and others known to those of skill in the art, can be used, alone or in combination. However, when petroleum chemistry is being evaluated, the product stream often does not include UV-active compounds. In this type of embodiment, the analytical equipment preferably includes an ELSD detector.

The entire eluent from the chromatographic columns described above can be sent through an appropriate detector and then to a mass spectrometer. When sample collection is desired, it can begin when the UV or mass spectrometry signal indicates the presence of the eluting compound, and can end when the UV signal indicates that the compound has finished eluting from the column. Mass spectrometry can verify that the eluted compound is really the compound of interest. Particularly when mono-olefins, di-olefins, oxygenates and paraffins are evaluated using the library, a combination of GC and MS is used, particularly since mono- and di-olefins may elute from the GC column at similar rates.

The device preferably includes a computer system capable of storing information regarding the identity of the ionic liquids, metal salts and the product streams obtained when combinations of ionic liquids and metal salts are used to separate the mono- and di-olefins from each other and optionally from non-olefins. Software for managing the data is stored on the computer.

Relational database software can be used to correlate the identity of the ionic liquids, the metal salts, and the analytical data from each product stream. Numerous commercially available relational database software programs are available.

Relational database software is a preferred type of software for managing the data obtained during the processes described herein. However, any software that is able to create a "memory map" of the ionic liquids in the tubes and correlate that information with the information obtained from the chemical reactions can be used. This type of software is well known to those of skill in the art.

The present invention will be better understood with reference to the following non-limiting examples.

EXAMPLE 1

Synthesis of Neutral Ionic Liquids

A variety of quaternary amine ionic liquid precursors were prepared as follows. 1-Methylimidazole was measured into a stainless-steel autoclave along with a slight molar excess of 1-chlorobutane. The autoclave was sealed, pressurized with 75 psig of nitrogen, and heated to 90° C. for 18 h. The autoclave was then cooled to room temperature and the contents were placed on a rotary evaporator at 95° C. for several hours to remove any unreacted chlorobutane and 1-methylimidazole. A $^1$H NMR of the product indicated the formation of 1-butyl-3-methylimidazolium chloride (bmim$^+$ Cl$^-$). The reaction was repeated with 1-chlorohexane to give 1-hexyl-3-methylimidazolium chloride (hmim$^+$Cl$^-$). This general procedure was repeated with pyridine to give the ionic liquid precursors N-butylpyridinium chloride (butpyr$^+$ Cl$^-$) and N-hexylpyridinium chloride (hexpyr$^+$Cl$^-$), although a higher reaction temperature (130° C.) was required to achieve high yields.

Two different procedures were used for conducting an anion exchange reaction to give a neutral ionic liquid. In one procedure, the precursor is dissolved in acetone and reacted with the sodium salt of the desired anion (NaBF$_4$ or NaPF$_6$). In the other procedure, the precursor is dissolved in water and reacted with the acid form of the anion (HBF$_4$ or HPF$_6$). The precursor hmim$^+$Cl$^-$ was used make the ionic liquid hmim$^+$PF$_6^-$ by both procedures. The miscibility of the resulting ionic liquid with water was greatly influenced by the route of synthesis. The ionic liquid made by the acid route was immiscible with water, while the ionic liquid made using the sodium salt was miscible with water. While not wishing to be bound to a particular theory, it is believed that this change in miscibility with water is due to the presence of residual NaCl in the liquid made via the salt route.

The acid procedure was then used to generate a variety of ionic liquids using the precursors synthesized above, as well as additional precursors purchased from commercial suppliers. These reactions are summarized in Table 1.

TABLE 1

Ionic Liquids

| Ionic Liquid Precursor | Anion Source | Ionic Liquid |
|---|---|---|
| Bmim$^+$Cl$^-$ | HBF$_4$ | Bmim$^+$ BF$_4^-$ |
| Bmim$^+$Cl$^-$ | HPF$_6$ | Bmim$^+$ PF$_6^-$ |
| Hmim$^+$Cl$^-$ | NaBF$_4$ | Hmim$^+$ BF$_4^-$ |
| Hmim$^+$Cl$^-$ | HBF$_4$ | Hmim$^+$ BF$_4^-$ |
| Hmim$^+$Cl$^-$ | NaPF$_6$ | Hmim$^+$ PF$_6^-$ |
| Hmim$^+$Cl$^-$ | HPF$_6$ | Hmim$^+$ PF$_6^-$ |
| Hexpyr$^+$Cl$^-$ | HBF$_4$ | Hexpyr$^+$ BF$_4^-$ |
| Hexpyr$^+$Cl$^-$ | HPF$_6$ | Hexpyr$^+$ PF$_6^-$ (mp = 38.7° C.) |
| (C$_8$H$_{17}$)$_3$MeN$^+$Cl$^-$ | HBF$_4$ | (C$_8$H$_{17}$)$_3$MeN$^+$ BF$_4^-$ (mp = 58.8° C.) |
| (C$_8$H$_{17}$)$_3$MeN$^+$Cl$^-$ | HPF$_6$ | (C$_8$H$_{17}$)$_3$MeN$^+$ PF$_6$ |
| Me$_3$NH$^+$Cl$^-$ | HBF$_4$ | Me$_3$NH $^+$BF$_4-$ (mp = 183° C.) |
| Bu$_2$Me$_2$N $^+$Cl$^-$ | HPF$_6$ | Bu$_2$Me$_2$N$^+$PF$_6^-$ (mp = 154.5° C.) |
| (C$_{16}$H$_{33}$)Me$_3$N$^+$Cl$^-$ | HPF$_6$ | (C$_{16}$H$_{33}$)Me$_3$N$^+$PF$_6^-$ (mp = 131.7° C.) |
| Bu$_2$Me$_2$N $^+$Cl$^-$ | HBF$_4$ | Bu$_2$Me$_2$N $^+$ BF$_4^-$ (mp = 75.1° C.) | bmim = 1-butyl-3-methylimidazolium
hexpyr = N-hexylpyridinium
hmim = 1-hexyl-3-methylimidizolium

EXAMPLE 2

Solubility of Cu and Ag complexes in Ionic Liquids

The present example investigated the possibility of immobilizing Ag and Cu ions in an ionic liquid. The Ag(I) and Cu(I) compounds have been proposed for use in the selective complexation of dienes over mono-olefins. The immobilization of these ions can be accomplished by either dissolving Ag and Cu salts in an existing ionic liquid or by reacting an ionic liquid precursor with a Ag or Cu complex to create a new ionic liquid.

Several screening reactions were conducted to determine whether Ag and Cu complexes were soluble in ionic liquids. The results are summarized in Table 2.

TABLE 2

Solubility of Ag and Cu ion in ionic liquids

| Ionic Liquid or Precursor | Salt | Soluble? |
|---|---|---|
| Bmim$^+$BF$_4^-$ | AgBF$_4$ | Yes |
| Bmim$^+$PF$_6^-$ | AgPF$_6$ | No |
| Bmim$^+$Cl$^-$ | AgCl | No |
| Hmim$^+$Cl$^-$ | AgCl | No |
| Hexpyr$^+$Cl$^-$ | AgCl | No |
| Bmim$^+$Cl$^-$ | CuCl | Yes |
| Hmim$^+$Cl$^-$ | CuCl | Yes |
| Hexpyr$^+$Cl$^-$ | CuCl | Yes |

As shown above, an attempt was made to dissolve the Ag salts in ionic liquids that contained the same anions. For example, AgBF$_4$ was combined with bmim$^+$BF4$^-$ and AgPF$_6$ was combined with bmim$^+$PF$_6^-$. AgBF$_4$ was soluble in the ionic liquid. Neither AgPF$_6$ nor AgCl dissolved in the ionic liquids that were tested. Attempts were made to dissolve CuCl in a couple of different ionic liquids and ionic liquid precursors. The CuCl dissolved in bmim$^+$Cl$^-$, hmim$^+$ Cl$^-$, and hexpyr$^+$Cl$^-$. It is believed that the CuCl participated in a complexation reaction to give new ionic liquids with CuCl$_2^-$ anions.

EXAMPLE 3

Use of ionic Liquids Containing Aq(I) and Cu(I) Salts for Diene Coordination

This example evaluated the use of Ag(I) and Cu(I) compounds immobilized in ionic liquids for the selective complexation of dienes. The adsorption of 1-butene gas by the ionic liquid samples was measured and is summarized in Table 3. The ionic liquid samples containing varying amounts of dissolved AgBF$_4$ showed reversible absorption of the butene gas while the ionic liquids containing the CuCl$_2^-$ anion did not show any appreciable absorption. For the Ag-containing ionic liquids, the ratio of butene absorbed to Ag was slightly higher than 1. This suggests that the Ag coordinates more than one olefin at a time which would make an Ag-diene complex more thermodynamically stable. Therefore, these Ag-containing ionic liquids are able to selectively coordinate dienes over mono-enes.

As a control experiment, the Ag-containing ionic liquids were also tested for butane absorption. No appreciable absorption was detected. This again suggests that the Ag is forming a complex with the olefin and that the gases are not merely dissolving in the ionic liquid.

TABLE 3

Gas Absorption by Ionic Liquids Containing Ag(I) and Cu(I) salts.

| Ionic Liquid | Salt | Gas | Wt % Gas Absorbed | Mols Gas/ mols M(I) |
|---|---|---|---|---|
| Bmim$^+$BF$_4^-$ | 5% AgBF$_4$ | 1-butene | 1.45 | 1.32 |
| Bmim$^+$BF$_4^-$ | 10% AgBF$_4$ | 1-butene | 1.89 | 0.87 |
| Bmim$^+$BF$_4^-$ | 25% AgBF$_4$ | 1-butene | 7.69 | 1.30 |
| Bmim$^+$Cl$^-$ | 1.0 equiv CuCl | 1-butene | 0.03 | Nc |

TABLE 3-continued

Gas Absorption by Ionic Liquids Containing Ag(I) and Cu(I) salts.

| Ionic Liquid | Salt | Gas | Wt % Gas Absorbed | Mols Gas/ mols M(I) |
|---|---|---|---|---|
| Bmim$^+$Cl$^-$ | 2.0 equiv CuCl | 1-butene | 0.15 | Nc |
| Hexpyr$^+$Cl$^-$ | 1.0 equiv CuCl | 1-butene | 0.60 | Nc |
| Bmim$^+$BF$_4^-$ | 5% AgBF$_4$ | Butane | 0.13 | 0.10 |
| Bmim$^+$BF$_4^-$ | 10% AgBF$_4$ | Butane | 0 | 0 |
| Bmim$^+$BF$_4^-$ | 25% AgBF$_4$ | Butane | 2.56 | 0.35 | bmim = 1-butyl-3-methylimidazolium;
hexpyr = N-hexylpyridium;
nc = not calculated Next, a mixture of hexene and 1,5 hexadiene was mixed in n-decane and exposed to four ionic liquid solutions. The ionic liquid solutions were 1-butyl-3-methyl-imidazolium tetrafluoroborate (Bmim$^+$BF4$^-$) mixed with 0%, 5%, 10%, and 25% AgBF$_4$ to form silver containing ionic liquids. The results showed a preference for adsorbing the 1,5 hexadiene over the hexene. The results are shown in Table 4.

TABLE 4

Selective Absorption of dienes over mono-olefins

| | Mol Hexene/ mol Ag$^+$ | Mol Hexadiene/ mol Ag$^+$ | Hexadiene/ hexene |
|---|---|---|---|
| 0% AgBF$_4$ | N/A | N/A | 1.66 |
| 5% AgBF$_4$ | 0 | 1.4 | N/A |
| 10% AgBF$_4$ | 0.27 | 1.1 | 4.0 |
| 25% AgBF$_4$ | 0.42 | 1.1 | 2.6 |

The ionic liquids also show an affinity for adsorption of dienes over alpha olefins, and alpha olefins over paraffins. The same ionic liquids were run in a TGA (total gas adsorption) system to measure the uptake of butane, butene, and 1,3 butadiene. The liquids show very little uptake of the butane because it contains no double bonds to interact with the Ag$^+$. Higher uptakes of the olefins showed the ability of metal infused ionic liquids to serve as adsorbents. The results are shown below in Table 5.

TABLE 5

Selective Absorption of dienes over mono-olefins over paraffins

| | Mol butane/ mol Ag$^+$ | Mol butene/ mol Ag$^+$ | Mol 1,3-butadiene/ mol Ag$^+$ |
|---|---|---|---|
| 5% AgBF$_4$ | 0.1 | 1.3 | 3.7 |
| 10% AgBF$_4$ | 0 | 0.8 | 2.3 |
| 25% AgBF$_4$ | 0.2 | 1.3 | 1.3 |

Next, a mixture of hexene and 1,5 hexadiene was mixed in n-decane and exposed to an ionic liquid solution containing a copper triflate. The ionic liquid solution was 1-butyl-3-methyl-imidazolium/copper trifluoromethanesulfonate (Bmim/CuOTf). The results showed a preference for adsorbing the 1,5 hexadiene over the hexene. The results are shown in Table 6.

TABLE 6

Selective Absorption of dienes over mono-olefins

| | Mol hexene/ mol Cu$^+$ | Mol hexadiene/ mol Cu$^+$ | Mol hexadiene/ mol hexene |
|---|---|---|---|
| 10% CuOTf | 0.072 | 0.367 | 5.13 |

Next, a mixture of hexene and 1,5 hexadiene was mixed in n-decane and exposed to Bmim/CuOTf wherein the triflate had been slightly air exposed. Two samples were run, both with and without hydrogen exposure. The results again showed a preference for adsorbing the 1,5 hexadiene over the hexene. Furthermore, there was no decrease in diene loading or selectivity in the hydrogen exposed sample. The results are shown in Table 7.

TABLE 7

Selective Absorption of dienes over mono-olefins

| | Mol hexene/ mol Cu$^+$ | Mol hexadiene/ mol Cu$^+$ | Mol hexadiene/ mol hexene |
|---|---|---|---|
| No H$_2$ Exposure 10% CuOTf | 0.073 | 0.284 | 3.91 |
| H$_2$ Exposure 10% CuOTf | 0.077 | 0.291 | 3.80 |

While not wishing to be bound to any particular theory, it is believed that the decrease in diene loading in the air exposed sample (compared with the non-air exposed sample) is due to partial deactivation of the Cu due to O$_2$ exposure. Notably, no decrease was observed due to H$_2$ exposure. It is also believed that the lack of appreciable uptake of diene by the ionic liquids containing copper salts shown in Table 3 was due to the formation of a new ionic liquid, Bmim$^+$CuCl$_2^-$, wherein the copper is tied up in the anion and, as such, not available for complexation.

Additionally, TGA adsorption experiments were conducted on each of the ionic liquids described above with butane and 1-butene under the following test conditions: sample size: approximately 20 mg; C$_4$ flow rate: 50 cc/min; temperature: isothermal at −24° C. The TGA recorded the sample weight until a plateau was reached in the sample weight versus time plot. Three of the samples displayed significant amounts of butane and 1-butene adsorption and were further tested with 1,3-butadiene. Additional adsorption experiments were conducted using 1,7 octadiene, 1-octene, and 1,9 decadiene. The C$_8$-diolefin and C$_{10}$-diolefin runs were done with a new batch of 10% AgBF$_4$ imidazolium ionic liquid, so a C$_6$-diolefin was run for comparison with previous results. The results show that the ionic liquids selectively adsorb out the alpha-omega diene over the paraffin and normal alpha olefins (NAOs).

A mixture of 1,7 octadiene and 1-octene (about 3.2 wt % each in n-decane) was evaluated. The resulting liquid after 24 hours in mixing contact with the ionic liquid contained the same amount of 1-octene, but only 1.4 wt % of the 1,7 octadiene. This corresponds to an adsorption of 0.72 moles C$_8$-diene/mole Ag$^+$, slightly lower than previous experiments showed for C$_6$-diene, and demonstrates that the C$_8$-diene is preferentially adsorbed over the C$_8$-mono-olefin.

A mixture of C$_{10}$-diolefin in decane (4.2 wt %) was also run and showed a decrease to 0.7 wt % after 24 hours. This corresponds to an adsorption ratio of 1.2 mol C$_{10}$-diolefin/ mol Ag$^+$.

A mixture of a C$_6$-diolefin, a C$_8$-diolefin and a C$_{10}$-diolefin was subjected to the same conditions. The C$_6$-diolefin was preferentially adsorbed over the C$_8$-diolefin and the C$_{10}$-diolefin. While not wishing to be bound to a particular theory, it is believed that the differential adsorption is due to differences in solubility.

Ionic liquids can be used to improve the separation of diolefins (alpha-omega olefins) from normal alpha olefins (NAOs). The ionic liquids which have been tested are mixtures that contain an organic amine and a transition metal compound. Because ionic liquids readily separate from hydrocarbons and are thermally stable over a wide temperature range, they can be used in an extractive distillation or liquid-liquid extraction separation process. The process can therefore be used to purify large amounts of NAOs, which are typically used as chemical precursors for the synthesis of polyethylenes, surfactants, synthetic lubricants and additives, etc.

It will be apparent to those skilled in the art of chemical separations that the process of this invention can be applied to a wide variety of mixtures of mono-olefins, di-olefins, and/or non-olefins, and the forgoing examples are intended to be illustrative and non-limiting. Those skilled in the art of chemical separations can readily determine the operative and optimal ionic liquids, metal salt and conditions for carrying out the processes and process steps of this invention for any specific separation of mono-olefins, di-olefins and/or non-olefins using the combinational chemistry approaches herein and other techniques known in the art.

What is claimed is:

1. A method for separating mono-olefins comprising:
   a) contacting a mixture comprising di-olefins and mono-olefins with an olefin-complexing metal salt dissolved, dispersed, or suspended in an ionic liquid;
   b) maintaining such mixture in contact with such olefin-complexing metal salt for sufficient time to selectively complex the di-olefins over the mono-olefins to form a metal salt/olefin complex; and
   c) separating the non-complexed mono-olefins.

2. The method of claim 1, further comprising desorbing the di-olefins from the metal salt/olefin complex.

3. The method of claim 2, wherein said ionic liquid is capable of forming a solution, suspension or dispersion with said olefin-complexing metal salt.

4. The method of claim 3, wherein the amount of said olefin-complexing metal salt is adjusted so as to complex essentially only the di-olefins.

5. The method of claim 1, wherein the metal salt comprises a Group IB metal.

6. The method of claim 5, wherein the metal salt is a copper salt.

7. The method of claim 6, wherein the metal salt is CuOTf.

8. The method of claim 5, wherein the metal salt is a silver salt.

9. The method of claim 8, wherein the metal salt is AgBF$_4$.

10. The method of claim 1, wherein the mono-olefin and di-olefin-containing mixture is a gaseous olefin-containing stream.

11. The method of claim 1, wherein said mixture is contacted with said olefin-complexing metal salt in a distillation apparatus.

12. The method of claim 11, further comprising separating said non-complexed mono-olefins by distillation in said distillation apparatus.

13. The method of claim 12, further comprising desorbing said di-olefins from said metal salt/olefin complex by distillation in said distillation apparatus.

14. The method of claim 1, wherein said mixture is contacted with said olefin-complexing metal salt in a system of one or more liquid mixers.

15. The method of claim 14, further comprising separating said non-complexed mono-olefins from said metal salt/olefin complex by decantation.

16. The method of claim 15, further comprising desorbing said di-olefins from said metal salt/olefin complex in a regeneration apparatus.

17. The method of claim 16, further comprising sending the bottoms from said regeneration apparatus to said system of liquid mixers.

18. The method of claim 1, wherein the mixture of mono- and di-olefins is derived from wax hydrocracking, paraffin dehydrogenation, or combinations thereof.

19. The method of claim 1, further comprising subjecting the mixture to partial hydrogenation prior to the contacting step.

20. A method for separating mono-olefins comprising:
   a) contacting a mixture comprising di-olefins and mono-olefins with an olefin-complexing metal salt dissolved, dispersed, or suspended in an ionic liquid;
   b) maintaining such mixture in contact with such olefin-complexing metal salt for sufficient time to complex the mono-olefins and di-olefins with the olefin-complexing metal salt to form a metal salt/olefin complex; and
   c) selectively desorbing the mono-olefins from the metal salt/olefin complex.

21. The method of claim 20, further comprising desorbing the di-olefins from the metal salt/olefin complex.

22. A method for separating mono-olefins and/or di-olefins comprising:
   a) contacting a mixture comprising di-olefins, mono-olefins and non-olefins with an olefin-complexing metal salt dissolved, dispersed or suspended in an ionic liquid;
   b) maintaining such mixture in contact with such olefin-complexing metal salt for sufficient time to complex the mono-olefins and di-olefins with the olefin-complexing metal salt to form a metal salt/olefin complex;
   c) separating the non-complexed non-olefins; and
   d) selectively desorbing the mono-olefins from the metal salt/olefin complex.

23. The method of claim 22, further comprising desorbing the di-olefins from the metal salt/olefin complex.

24. The method of claim 23, wherein said ionic liquid is capable of forming a solution, suspension or dispersion with said olefin-complexing metal salt.

25. The method of claim 22, wherein the metal salt comprises a Group IB metal.

26. The method of claim 25, wherein the metal salt is a copper salt.

27. The method of claim 26, wherein the metal salt is CuOTf.

28. The method of claim 25, wherein the metal salt is a silver salt.

29. The method of claim 28, wherein the metal salt is AgBF$_4$.

30. The method of claim 22, wherein the non-olefins comprise at least one of paraffins, oxygenates, aromatics, or mixtures and combinations thereof.

31. The method of claim 30, wherein the paraffins comprise cycloparaffins.

32. The method of claim 22, wherein the mono-olefins comprise at least one of ethylene, propylene, or mixtures and combinations thereof.

33. The method of claim 32, wherein the ethylene is produced in an ethylene cracker, an EP cracker, a naphtha cracker, or combinations thereof.

34. The method of claim 22, wherein the olefins are produced in an apparatus selected from the group consisting of an FCC unit, naphtha hydrotreater, catalytic reformer, distillate hydrotreter, hydrocracker, coker, RFCC unit, RDS unit and combinations thereof.

35. The method of claim 22, wherein the olefins are derived from paraffin dehydrogenation, ethylene oligomerization, wax hydrocracking, or combinations thereof.

36. The method of claim 22, wherein the olefins are produced in a Fischer-Tropsch synthesis.

37. The method of claim 22, wherein the mono-olefins are normal alpha olefins derived from the ethenolysis of heavier internal olefins.

38. The method of claim 22, wherein the olefins are separated from a recycle stream in a Fischer-Tropsch synthesis to reduce the amount of olefins recycled from a Fischer-Tropsch unit to an upstream methane reformer.

39. The method of claim 22, wherein the olefin-containing mixture is a gaseous olefin-containing stream.

40. The method of claim 22, wherein said mixture is contacted with said olefin-complexing metal salt in a distillation apparatus.

41. The method of claim 40, further comprising separating said non-complexed non-olefins from said metal salt/olefin complex by distillation.

42. The method of claim 41, further comprising desorbing said mono-olefins from said metal salt/olefin complex by distillation in said distillation apparatus.

43. The method of claim 42, further comprising desorbing said di-olefins from said metal salt/olefin complex by distillation in said distillation apparatus.

44. The method of claim 22, wherein said mixture is contacted with said olefin-complexing metal salt in a system of one or more liquid mixers.

45. The method of claim 44, further comprising separating said non-complexed non-olefins from said metal salt/olefin complex by decantation.

46. The method of claim 45, further comprising desorbing said mono-olefins from said metal salt/olefin complex in a regeneration apparatus.

47. The method of claim 46, further comprising desorbing said di-olefins from said metal salt/olefin complex in said regeneration apparatus.

48. The method of claim 47, further comprising sending the bottoms from said regeneration apparatus to said system of liquid mixers.

49. The method of claim 22, further comprising purifying the olefin-containing mixture before the contacting step to remove sulfur, acetylinics, oxygenates, and other heteroatoms.

50. A method for separating mono-olefins and/or di-olefins comprising:
  a) contacting a mixture comprising di-olefins, mono-olefins and non-olefins with an olefin-complexing metal salt dissolved, dispersed or suspended in an ionic liquid;
  b) maintaining such mixture in contact with such olefin-complexing metal salt for sufficient time to selectively complex the di-olefins over the mono-olefins to form a first metal salt/olefin complex;
  c) separating the non-complexed mono-olefins and non-olefins;
  d) desorbing the di-olefins from the first metal salt/olefin complex;
  e) contacting the non-complexed mono-olefins and non-olefins with the olefin-complexing metal salt;
  f) maintaining such non-complexed mono-olefins and non-olefins in contact with such olefin-complexing metal salt for sufficient time to complex the mono-olefins to form a second metal salt/olefin complex; and
  g) separartating the non-complexed non-olefins.

51. The method of claim 50 further comprising desorbing the mono-olefins from the second metal salt/olefin complex.

52. The method of claim 51, wherein the amount of said olefin-complexing metal salt is adjusted so as to complex essentially only the di-olefins.

53. The method of claim 1, wherein said ionic liquid is comprised of anions and cations, wherein;
  said anions are selected from the group consisting of halide salts, metal anions, chloroaluminate, bromoaluminate, gallium chloride, tetrafluoroborate, tetrachloroborate, hexafluorophosphate, nitrate, trifluoromethane sulfonate, methylsulfonate, p-toluenesulfonate, hexafluoroantimonate, hexafluoroarsenate, tetrachloroaluminate, tetrabromoaluminate, perchlorate, hydroxide anion, copper dichloride anion, iron trichloride anion, antimony hexafluoride, copper dichloride anion, zinc trichloride anion, lanthanum anion, potassium anion, lithium anion, nickel anion, cobalt anion, manganese anion, and combinations and mixtures thereof; and
  said cations are selected from the group consisting of cyclic and non-cyclic quaternary ammonium cations, alkylammoniums, pyridiniums, substituted pyridiniums, N-alkylpyridiniums, imidazoliums, substituted imidazoliums, N,N'-dialkylimidazoliums, pyrroliniums, substituted pyrroliniums, phosphoniums, alkylphosphoniums, arylphosphoniums, 1-butyl-3-methylimidazolium, N-hexylpyridinium, 1-hexyl-3-methylimidizolium, $(C_8H_{17})_3MeN$, $Bu_2Me_2N$, and mixtures and combinations thereof.

54. The method of claim 22, wherein said ionic liquid is comprised of anions and cations, wherein;
  said anions are selected from the group consisting of halide salts, metal anions, chloroaluminate, bromoaluminate, gallium chloride, tetrafluoroborate, tetrachloroborate, hexafluorophosphate, nitrate, trifluoromethane sulfonate, methylsulfonate, p-toluenesulfonate, hexafluoroantimonate, hexafluoroarsenate, tetrachloroaluminate, tetrabromoaluminate, perchlorate, hydroxide anion, copper dichloride anion, iron trichloride anion, antimony hexafluoride, copper dichloride anion, zinc trichloride anion, lanthanum anion, potassium anion, lithium anion, nickel anion, cobalt anion, manganese anion, and combinations and mixtures thereof; and
  said cations are selected from the group consisting of cyclic and non-cyclic quaternary ammonium cations, alkylammoniums, pyridiniums, substituted pyridiniums, N-alkylpyridiniums, imidazoliums, substituted imidazoliums, N,N'-dialkylimidazoliums, pyrroliniums, substituted pyrroliniums, phosphoniums, alkylphosphoniums, arylphosphoniums, 1-butyl-3-methylimidazolium, N-hexylpyridinium, 1-hexyl-3-methylimidizolium, $(C_8H_{17})_3MeN$, $Bu_2Me_2N$, and mixtures and combinations thereof.

55. A method for optimizing the method of claim 1, comprising preparing a combinatorial library including a plurality of combinations of ionic liquids and olefin-complexing metal salts, and evaluating the library for its ability to separate di-olefins from a mixture comprising mono-olefins and di-olefins.

56. A method for optimizing the method of claim 22, comprising preparing a combinatorial library including a plurality of combinations of ionic liquids and olefin-complexing metal salts, and evaluating the library for its ability to separate olefins from a mixture comprising olefins and non-olefins.

* * * * *